United States Patent [19]

Hollingsworth et al.

[11] Patent Number: 6,040,464
[45] Date of Patent: Mar. 21, 2000

[54] PROCESS FOR THE PREPARATION OF PROTECTED 3-AMINO-1,2-DIHYDROXYPROPANE ACETAL AND DERIVATIVES THEREOF

[75] Inventors: Rawle I. Hollingsworth, Haslett; Guijun Wang, East Lansing, both of Mich.

[73] Assignee: Board of Trustees operating Michigan State University, East Lansing, Mich.

[21] Appl. No.: 09/320,989

[22] Filed: May 27, 1999

Related U.S. Application Data

[60] Provisional application No. 60/087,496, Jun. 1, 1998.
[51] Int. Cl.⁷ .................................................. C07D 317/00
[52] U.S. Cl. .......................... 549/451; 549/514; 549/518; 568/844; 564/468; 564/487; 564/488
[58] Field of Search ...................................... 564/468, 487, 564/488; 568/844; 549/451, 514, 518

[56] References Cited

U.S. PATENT DOCUMENTS 5,292,939  3/1994  Hollingsworth .
5,319,110  6/1994  Hollingsworth .
5,374,773  12/1994  Hollingsworth .
5,808,107  9/1998  Hollingsworth .

OTHER PUBLICATIONS

Byun, H.–S, et al., J. Org. Chem. 59:668–671 (1994), Jun.
Bednarski, M.D., et al., J. Am. Chem. Soc. 109:1283–1285 (1987), Jun.
Fuganti, C., et al., Tetrahedron 44:2575–2582 (1988), Jun.
Chen, J., et al., Tetrahedron Lett. 34:7663–7666 (1993), Jun.
Baldwin, J. J., et al., J. Med. Chem. 25:931–936 (1982), Jun.
Danklmaier, J., et al., Liebigs Ann. Chem. 1149–1154 (1988), Jun.

*Primary Examiner*—Samuel Barts
*Attorney, Agent, or Firm*—Ian C. McLeod

[57] ABSTRACT

A process for producing protected 3-amino-1,2-dihydroxypropane acetal, particularly in chiral forms, for use as an intermediate in the preparation of various 3-carbon compounds which are chiral. In particular, the present invention relates to the process for preparation of 3-amino-1,2-dihydroxypropane isopropylidene acetal. The protected 3-amino-1,2-dihydroxypropane acetal is a key intermediate to the preparation of chiral 3-carbon compounds which in turn are intermediates to various pharmaceuticals.

19 Claims, 6 Drawing Sheets

13C-NMR

PROCESS FOR THE PREPARATION OF PROTECTED 3-AMINO-1,2-DIHYDROXYPROPANE ACETAL AND DERIVATIVES THEREOF

CROSS-REFERENCE TO RELATED APPLICATION

This application claims priority to U.S. Provisional Application Ser. No. 60/087,496, filed Jun. 1, 1998.

STATEMENT REGARDING FEDERALLY SPONSORED RESEARCH OR DEVELOPMENT

This invention was supported in part by a United States Department of Energy Grant No. DE-FG02-89ER14029. The U.S. government has certain rights in this invention.

BACKGROUND OF THE INVENTION

(1) Field of the Invention

The present invention relates to a process for the preparation of protected 3-amino-1,2-dihydroxypropane acetal, particularly in chiral forms, for use as an intermediate in the preparation of various 3-carbon compounds which are chiral. In particular, the present invention relates to the process for preparation of 3-amino-1,2-dihydroxypropane isopropylidene acetal. The invention is particularly useful for preparation of glycidol, 1-bromo-2,3-dihydroxypropane, or 3-amino-1,2-dihydroxypropane starting from 3-hydroxy-γ-butyrolactone.

(2) Background of the Invention

Chiral 3-carbon synthons are very important compounds because they are used in a variety of pharmaceuticals and material science applications ranging from beta-blocker drugs, phospholipid and glycolipid analogs, thromboxane synthase inhibitors, sulfolipids and liquid crystal materials. However, chiral 3-carbon synthons are extremely expensive. Three key 3-carbon building blocks are (R)-glycidol (2), (R)-1-bromo-2,3-dihydroxypropane (3) and (S)-3-amino-1, 2-dihydroxypropane (4).

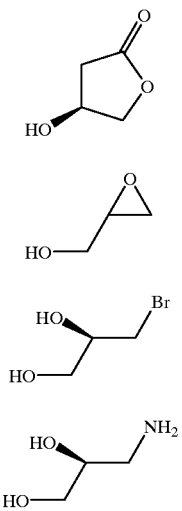

(R)-glycidol (2) and its (S)-isomer are much used intermediates in the synthesis of chiral compounds. Because of this, much effort has been expended in developing routes to them. These include catalytic oxidations with peroxides and chiral transition metal complexes (Byun, H. -S, et al., J. Org. Chem. 59:668–671 (1994)), enzymatic resolutions of racemic esters using lipases to selectively deacylate one member enantiomer (Bednarski, M. D., et al., J. Am. Chem. Soc. 109:1283–1285 (1987); Fuganti, C., et al., Tetrahedron 44:2575–2582 (1988); and Chen, J., et al., Tetrahedron Lett. 34:7663–7666 (1993)), and treatment of a chiral 1,2-propane diol with a leaving group such as a halide or tosylate ester in the 3-position with base (Baldwin, J. J., et al., J. Med. Chem. 25:931–936 (1982)). The availability of an easy route to 3 is therefore de facto a route to 2. The aminodiol 4 is a substructure that appears in a large class of important drugs especially the β-blockers such as Propanalol (5) and Metoprolol (6), the antiviral agent (7) and the thromboxane synthase inhibitor (8).

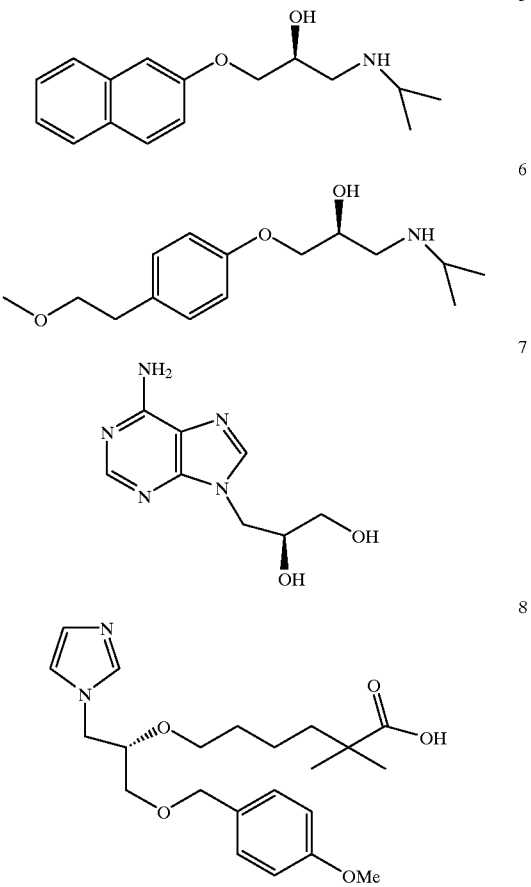

Thus, there is a need for a process to make chiral 3-carbon synthons which is inexpensive, safe, and easy to perform. In particular, it is desirable to have a process for making chiral 3-carbon synthons from renewable natural resources.

SUMMARY OF THE INVENTION

The present invention relates to a process for preparing a protected 3-amino-1,2-dihydroxypropane acetal in a Hoffman rearrangement reaction mixture, which comprises reacting a 4-carbon protected 1,2-dihydroxybutryamide in a Hoffman rearrangement reaction mixture with a hypohalite in the presence of a base in a solvent for the reaction mixture to produce the 3-carbon protected 3-amino-1,2-dihydroxypropane acetal. The process uses 3-hydroxy-γ-butyrolactone as the starting material. The protected 3-amino-1,2-dihydroxypropane is a useful intermediate for the synthesis of 3-carbon chiral compounds important for the manufacture of pharmaceuticals.

In particular the present invention relates to a process wherein 3-hydroxy-γ-butyrolactone is converted to an amide which is then converted to a protected butyramide using 2,2-dimethylpropane as the protecting group. The protected butyramide is then converted to 3-amino-1,2-dihydroxypropane isopropylidene acetal which is a precursor for the synthesis of other 3-carbon compounds such as glycidol, 1-halo-2,3-dihydroxypropane, and 3-amino-1,2-dihydroxypropane.

Thus, the present invention provides a process for preparing 3-carbon compounds which are useful for the manufacture of a variety of pharmaceutical compounds. The process uses as the starting material, 3-hydroxy-γ-butyrolactone (1) which is a renewable natural resource that is obtainable from starch, lactose, maltodextrins and other readily available carbohydrate feedstock.

OBJECTS

It is therefore an object of the present invention to provide a process for the production of protected 3-amino-1,2-dihydroxypropane acetals, in particular 3-amino-1,2-dihydroxypropane isopropylidene acetal which is an intermediate to the desired 3-carbon synthons 2, 3 and 4, preferably in chiral form from 1. It is also an object of the present invention to provide a process which is simple and economical. These and other objects will become increasingly apparent by reference to the following description and the drawings.

DESCRIPTION OF PREFERRED EMBODIMENTS

Figure 1:
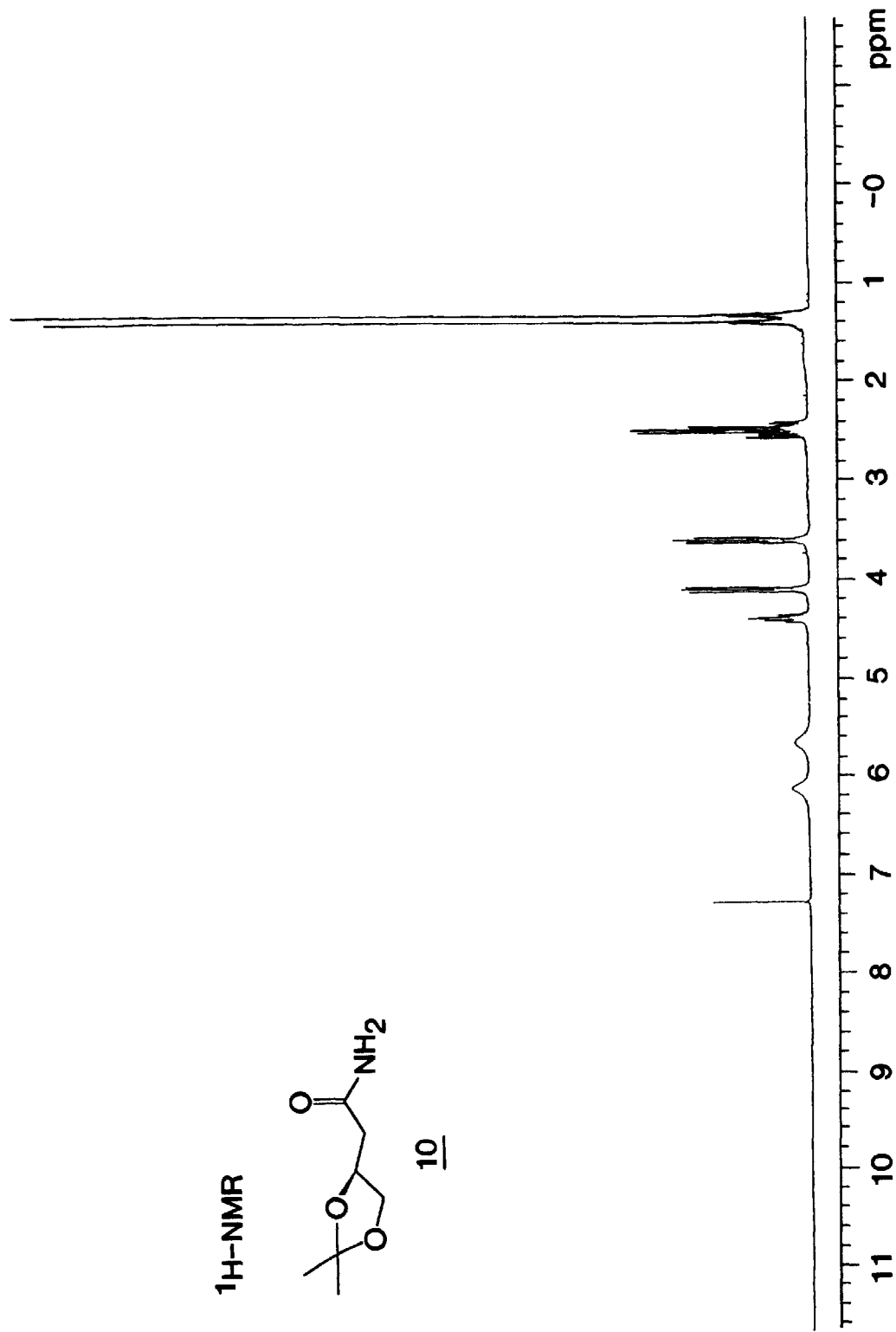
FIG. 1 is a $^1$H-NMR profile of a species of the protected butyramide, 3,4-dihydroxybutyramide isopropylidene acetal (10).

The present invention relates to a process for preparing a protected 3-amino-1,2-dihydroxypropane acetal in a Hoffman rearrangement reaction mixture, having the formula:

wherein $R_1$ and $R_2$ are protecting groups which can be combined which comprises reacting a protected 2,3-dihydroxybutryamide in a reaction mixture, having the formula:

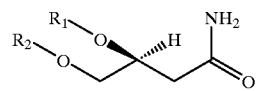

wherein $R_1$ and $R_2$ are the same protecting groups with a hypohalite in the presence of a base in a solvent for the reaction mixture to produce the protected 3-amino-1,2-dihydroxypropane acetal.

In the process, the protected 3,4-dihydroxybutyramide is produced from 3,4-dihydroxybutyramide in a reactive mixture which comprises an acid and a protecting group in a solvent for the reaction to produce the protected 3,4-dihydroxybutyramide. Furthermore, in the process the 3,4-dihydroxybutyramide is produced from 3-hydroxy-γ-butyrolactone in a reactive mixture comprising ammonia in a solvent for the reaction to produce the protected 3,4-dihydroxybutyramide. In the preferred process the 3-hydroxy-γ-butyrolactone and protected 3-amino-1,2-dihydroxypropane acetal produced are chiral. The process can use protecting groups selected from the group consisting of alkyloxy, aryloxy, acyloxy, halo, sulfonyloxy, sulfate, phosphate, saccharide and combinations thereof. In particular, the protecting group is an acetal selected from the group consisting of alkylidene, arylidene, acylidene and combinations thereof. In a preferred embodiment, the protecting group is a geminal dimethoxy-acetal.

The present invention further relates to the production of 3-carbon intermediates useful manufacture of pharmaceutical compounds. In particular, the production of 3-amino-1,2-dihydroxypropane wherein the protected 3-amino-1,2-dihydroxypropane acetal produced is further reacted to an acid which produces the 1-amino-2,3-dihydroxypropane; the production of 1-halo-2,3-dihydroxypropane wherein the protected 3-amino-1,2-dihydroxypropane acetal produced is further reacted with a halide source and a nitrite in the presence of an acid to produce the 1-halo-2,3-dihydroxypropane; or the production of 2,3-epoxy wherein in addition the 1-halo-2,3-dihydroxypropane is reacted with a base to form chiral 2,3-epoxy-1-hydroxypropane. In the preferred process the protected 3-amino-1,2-dihydroxypropane acetal is chiral and is converted as above to chiral 3-amino-1,2-dihydroxypropane or chiral 1-halo-2,3-dihydroxypropane are chiral. In the process for producing l-halo-2,3-dihydroxypropane the halo is selected from the group consisting of Cl, Br, I and F.

In a preferred process, the present invention relates to a process which comprises: (a) reacting 3-hydroxy-γ-butyrolactone with ammonia to produce 3,4-dihydroxybutyramide; (b) reacting the 3,4-dihydroxybutyramide with acetone and dimethyoxypropane in the presence of an acid to produce 3,4-dihydroxybutyramide isopropylidene acetal; and (c) reacting the 1,2-dihydroxybutyramide isopropylidene acetal with an hypohalite in the presence of a base to produce 3-amino-1,2-dihydroxypropane isopropylidene acetal.

The process uses chiral 3-hydroxy-γ-butyrolactone as the starting material so that the product will be chiral. The use of (S)-3-hydroxy-γ-butyrolactone (1) as the starting material for synthesis of 5 is convenient over prior art methods because 1 can be synthesized in high yield and in large quantities from renewable, natural resources. Inexpensive methods for synthesizing 1 have been described in: U.S. Pat. No. 5,319,110 to R. Hollingsworth which discloses a process for synthesis of an internal cyclic ester such as a lactone by converting a hexose source, which contains hexose as a substituent and another sugar attached to the hexose substituent in the 4 position via (S)-3,4-dihydroxybutanoic acid as an intermediate; U.S. Pat. No. 5,374,773 to R. Hollingsworth which discloses a process for the synthesis (S)-3,4-dihydroxybutanoic salt by converting a hexose source which contains hexose as a substituent and another sugar attached to the hexose substituent in the 4 position via (S)-3,4-dihydroxybutyric acid as an intermediate; U.S. Pat. No. 5,292,939 to R. Hollingsworth which discloses synthesis of (S)-3,4-dihydroxybutyric acid from substituted D-hexose; and U.S. Pat. No. 5,808,107 to R. Hollingsworth which discloses another process for producing chiral lactones. These references are herein incorporated by reference.

The general pathway for the synthesis of protected 3-amino-1,2-dihydroxypropane acetal is shown in Scheme 1.

that participation of the alcohol functions can be avoided by tying up the interfering alcohol functions with blocking or protecting groups. The 3 and 4 hydroxyl groups of the dihydroxybutyramide (9) can be protected with any combination of protecting groups which includes but is not limited to the constituents of the group consisting of alkyloxy, aryloxy, acyloxy, halo, sulfonyloxy, sulfate, phosphate or saccharide. In particular, the groups may be any combination of alkylidene, arylidene or acylidene groups which includes such acetals such as propylidene, benzylidene, ethylidene and methylidene. In a preferred embodiment, the protecting group is a geminal dimethoxy-acetal such as 2,2-dimethoxypropane which forms a cyclic acetal with the 3 and 4 hydroxyl groups of the dihydroxybutyramide (9) to form the protected dihydroxybutyramide (10A).

Scheme 2 shows the preferred synthesis of 3-amino-1,2-dihydroxypropane isopropylidene acetal (11) and 3-carbon chiral intermediates.

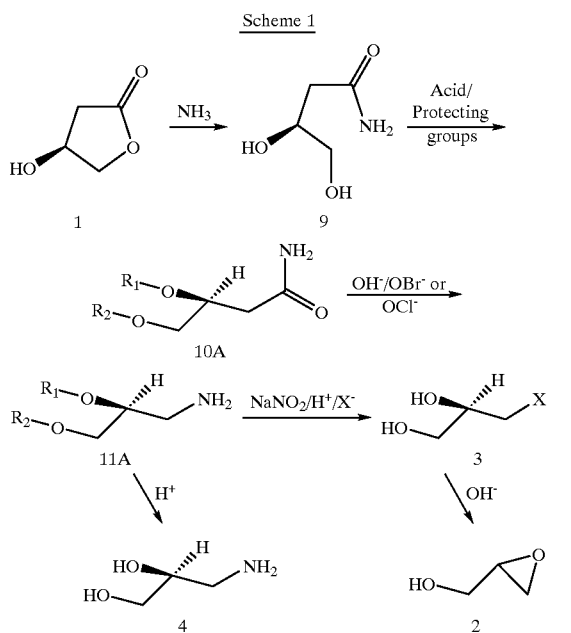

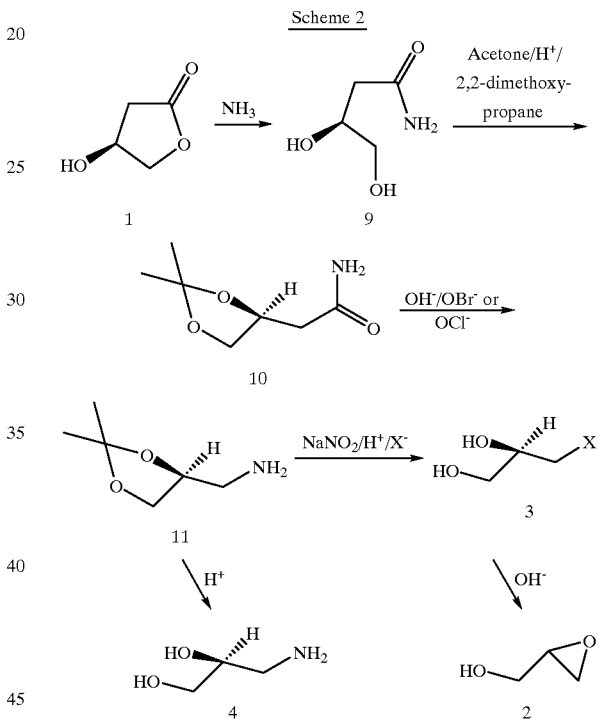

In Scheme 1, R1 and R2 are protecting groups which are acetals, and X is a halide selected from the group consisting of Cl, F, Br, and I. In the process 3-hydroxy-γ-lactone (1) is reacted in a reaction mixture with ammonia which produces the 1,2-dihydroxybutyramide (9). To effect the transformation of the 4-carbon (S)-3-hydroxy-γ-butyrolactone (1) to the 3-carbon compounds, it first has to be converted to a protected dihydroxybutyramide (10A). The butyramide is then converted to a protected 3-carbon amine (11A) by treatment with hypohalite ion in the presence of hydroxide ion. The protected amine is then deprotected with an acid to give 4 or converted to a halo diol such as 3 by treatment with nitrous acid and halide ion. There are several established methods for converting 3 to the epoxyalcohol 2.

The important step in obtaining 11A is a 1-carbon chain descension step in which the 4-carbon protected dihydroxybutyramide (10A) is stereospecifically and quantitatively converted to the pure 3-carbon primary amine (11A) via a Hoffman rearrangement reaction on the protected amide (10A). In a Hoffman rearrangement reaction, primary amides react with OCl⁻ or OBr⁻ in the presence of a strong base to form amines with the loss of the carbonyl carbon atom. However, such a reaction on a γ-hydroxyamide normally fails because of participation by the alcohol function to form a lactone. One important aspect of this invention is In Scheme 2, X is a halogen such as chlorine, iodine, fluorine or bromine. In the process, 3-hydroxy-γ-butyrolactone (1) is converted to 3,4-dihydroxybutyramide (9) in a reaction with ammonium hydroxide at room temperature. The reaction of the 3-hydroxy-γ-butyrolactone with ammonia in step (a) is preferably in aqueous solution at temperatures between −70° C. and 100° C. The ammonia is preferably between 1 and 4 molar equivalents, optimally 1.2. The water is removed preferably at reduced pressures (10 to 30 mm of Hg) at 30° to 50° C. After removal of water, 9 is converted to the protected butyramide (10) in a reaction mixture containing a protecting group such as 2,2-dimethoxypropane, and an acid in a solvent such as acetone. In particular, 9 is reacted with acetone and dimethoxypropane in the presence of a strong acid (sulfuric, hydrochloric, phosphoric, toluene sulfonic acid) at 15° to 70° C. for at least 30 minutes and then held at 20 to 25° C. for about 6 to 12 hours. Silver oxide is added to eliminate the acid. Any compatible neutralizing agent can be used. The mixture is filtered and then it is concentrated to dryness to produce 2,3- dihydroxybutyramide isopropylidene acetal 10. This reaction is quantitative and produces the protected butyramide (10) which can be crystallized upon concentration to dryness. A Hoffman rearrangement reaction completely converts 10 to 3-amino-1,2-dihydroxypropane isopropylidene acetal (11). In particular, 10 is reacted with a hypohalite (Cl, I, or Br) in the presence of a base (preferably an alkali metal hydroxide such as sodium hydroxide, potassium hydroxide) with heating at a temperature between 40 and 70° C. to produce 3-amino-1,2-dihydroxy isopropylidene acetal 11 which is a key intermediate in the preparation of other compounds, particularly if the product is chiral. For example, 11 can be converted to 1-halo-2,3-dihydroxypropane halide (3) in a reaction containing an acid and the halide which can then be converted to an epoxylalcohol (2) in a reaction containing a base.

Alternatively, reacting 11 with an acid will convert the protected amide to 3-amino-1,2-dihydroxypropane (4).

The bromodiol ((R)-1-bromo-2,3-dihydroxypropane) can be readily converted to (R)-glycidol by treatment with silver oxide at room temperature in a polar aprotic solvent such as dimethylformamide or dimethylsulfoxide. The dihydroxyamide 9 can be protected with any acetal function including benzylidene, ethylidene, methylidene and propylidene. In addition, it may be protected by conversion to a cyclic carbonate by treatment with reagents such as phosgene, ethylchloroformate or the corresponding acyl imidazole.

In the present invention, the carbonyl carbon of 10, the protected form of 9, which is formed from the lactone (1) is removed via a Roffman rearrangement reaction. In preparing 3-carbon intermediates, the present invention has several advantages over the prior art. The major advantage is that 1 is readily available in high optical and chemical purity and the reagents employed in the 1-carbon descension are cheap and safe to handle. There are no environmentally undesirable materials such as heavy metal ions involved as in some prior art processes (Byun, Y. -S., et al., J. Org. Chem. 59:668–671 (1994)). The optical purity of the product is high unlike in some prior art methods (Byun, H. -S., et al., J. Org. Chem. 59:668–671 (1994); Bednarski, M. D., et al., J. Am. Chem. Soc. 109:1283–1285 (1987); Fuganti, C., et al., Tetrahedron 44:2575–2582 (1988); and Chen, J., et al., Tetrahedron Lett., 34:7663–7666 (1993)). Furthermore, unlike in the prior art, recovery is simple with just a solvent extraction required. Therefore, the instant process provides a process the synthesis of chiral 3-carbon synthons from chiral 3-hydroxy-γ-butyrolactone 1 which is virtually quantitative and avoids the use of expensive transition metal catalysts or enzymes as are used in the prior art. Furthermore, the process is inexpensive to perform and uses renewable natural resources such as starch, lactose, maltodextrins and other readily available carbohydrate feedstock.

The following examples are intended to promote a further understanding of the present invention.

EXAMPLE 1

Figure 2:
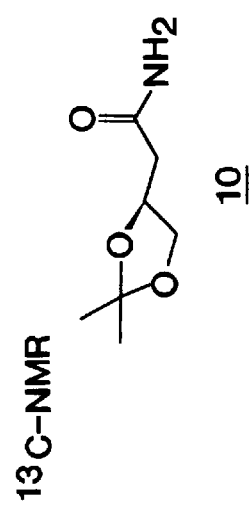
FIG. 2 is a $^{13}$C-NMR profile of a species of the protected butyramide, 2,3-dihydroxybutyramide isopropylidene acetal (10).
Figure 2:
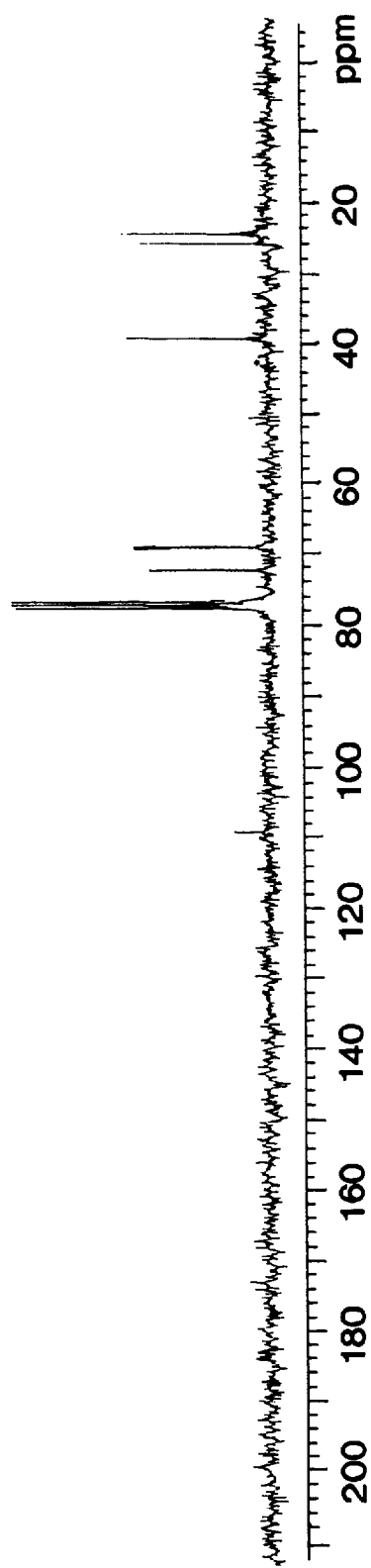

This Example shows the preparation of (S)-3-amino-1,2-dihydroxypropane isopropylidene acetal 11 from (S)-3-hydroxy-γ-butyrolactone 1. (S)-3-hydroxy-γ-butyrolactone (51 g, 0.5 mol) was converted to the amide 9 by treatment at room temperature for 14 hours with 110 ml of 30% ammonium hydroxide (0.85 mol). The solution was then concentrated to a syrup at ~50° C. under reduced pressure until no more water could be removed. Acetone (500 mL) and 2,2-dimethoxypropane (104 g, 1 mol) was added. Sulfuric acid (2 mL) was then added and the mixture protected from moisture with a calcium chloride drying tube, heated at 60° C. for 30 minutes and stirred at room temperature for 12 hours. Silver oxide (20 g) was added and the mixture stirred for 1 hour. Methanol (200 ml) was then added and the mixture filtered and concentrated to dryness. The amide (10) crystallized on concentrating and was used directly in the next step. Conversion was essentially quantitative. A small amount when recrystallized from acetone gave white crystals mp, 98–100° C. $[\alpha]_{589}$=−15.4 (CHCl$_3$, c=1), $^1$H-NMR (CDCl$_3$, 300 MHZ) δ 6.10 (s, 1H), 5.65 (s, 1H), 4.43 (m, 1H), 4.14 (dd, 1H, J=8.1 and 6.3 Hz) 3.63 (dd, 1H, J=8.1 and 6.8 Hz) 2.55 (dd, 1H, J=15.3 and 7.5 Hz), 2.46 (dd, 1H, J=15.3 and 4.8 Hz), 1.42 (s, 3H), 1.35 (s, 3H) $^{13}$C-NMR (CDCl$_3$, 75 MHZ) δ 172.86, 109.50, 72.21, 69.05, 40.07, 26.90, 25.50. FIGS. 1 and 2 show the H-NMR and 13C-NMR profiles, respectively, for 10.

Figure 3:
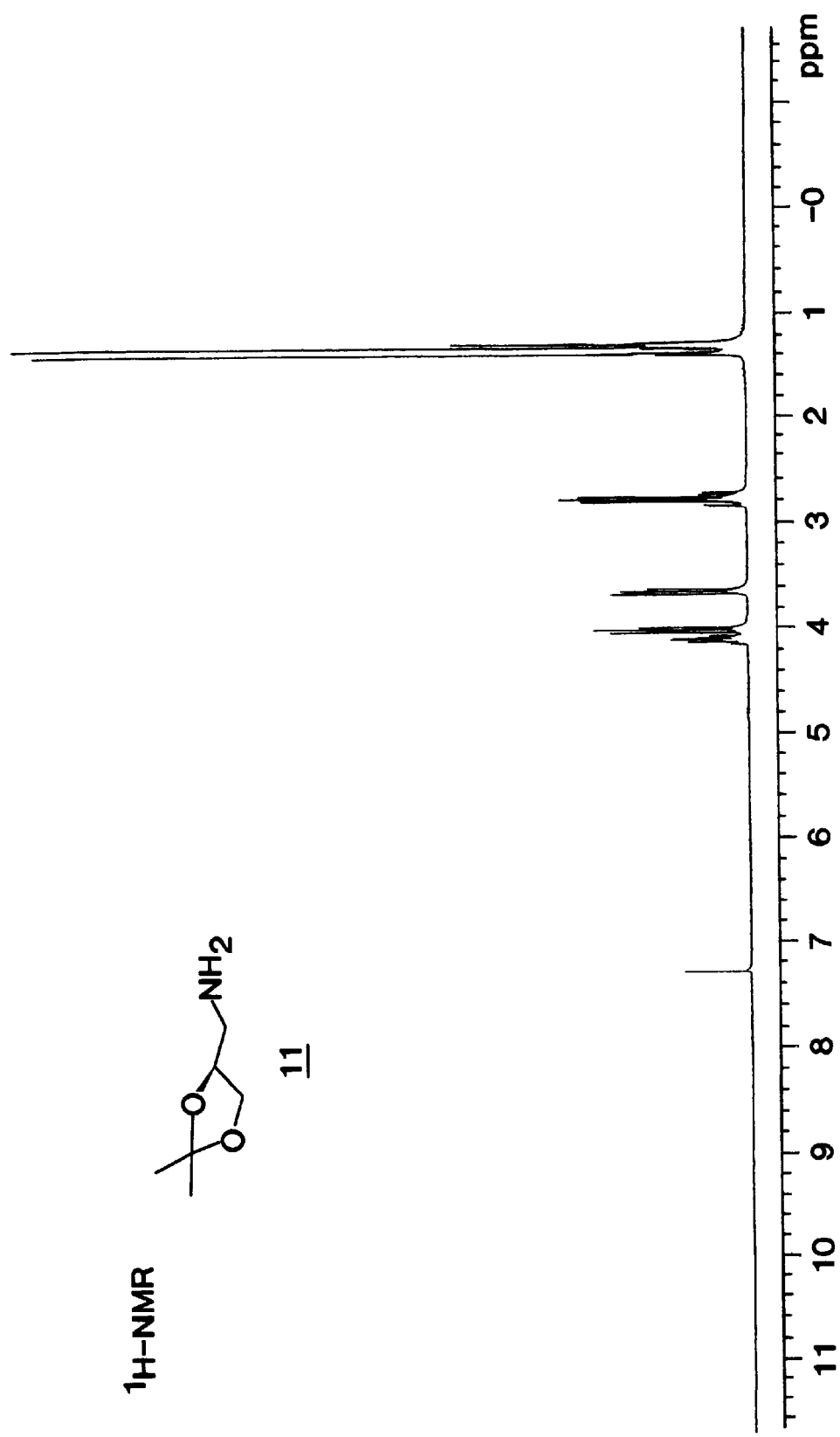
FIG. 3 is a 1H-NMR profile of a species of the protected 3-amino-1,2-dihydroxypropane, 3-amino-1,2-dihydroxypropane isopropylidene acetal (11).
Figure 4:
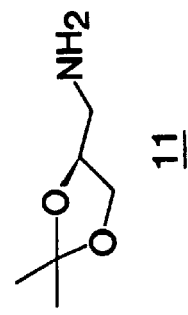
FIG. 4 is a $^{13}$C-NMR profile of a species of the protected 3-amino-1,2-dihydroxypropane, 1-amino-2,3-dihydroxypropane isopropylidene acetal (11).
Figure 4:
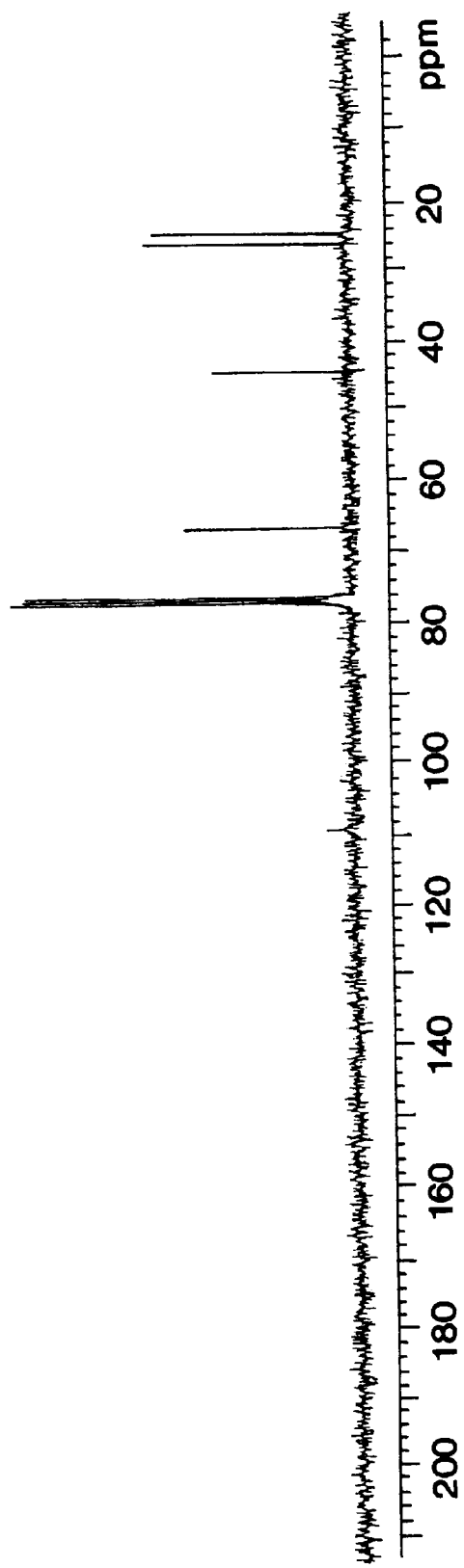

The amide (10) (1.59 g 0.01 mol) was treated with 10 to 12% sodium hypochlorite solution (10 ml) and the mixture stirred until all of the solid had dissolved (~5 mins). Sodium hydroxide (1.59 g dissolved in 10 ml water) was added to the mixture and the solution was warmed to 50–60° C. and then kept there for 24 hours by which time conversion to amine 11 completed. $^1$H-NMR spectroscopy indicated 100% conversion of 10 to 11. The amine 11 was isolated by extraction of the mixture with ether as a light yellow liquid which upon standing gave colorless crystals mp 54–56OC. The yield was 1.11 g (85%). The amine 11 has previously been reported to be liquid, bp 62–65° C., 15 torr (Danklmaier, J., Hoenig, H., Liebigs Ann. Chem. 1149–1154 (1988)) probably because it had not been isolated in as pure a state as reported herein. $[\alpha]_{589}$=+0.9 (CHCl$_3$, c=1), H-NMR (CDCl$_3$, 300 MHZ) δ 4.13 (m, 1H), 4.00 (dd, 1H, J=8.1 and 6.6 Hz), 3.67 (dd, 1H, J=8.1 and 6.3 Hz), 2.85 (dd, 1H, J=13.2 and 4.2 Hz), 2.78 (dd, 1H, J=13.2 and 6.0 Hz), 1.40 (s, 3H), 1.34 (s, 3H), 1.31 (s, 2H). $^{13}$C-NMR (CDCl$_3$ 75 MHZ) δ 109.10, 66.90, 44.71, 26.81, 25.31. FIGS. 3 and 4 show the $^1$H-NMR and $^{13}$C-NMR profiles, respectively, for

EXAMPLE 2

This Example demonstrates the conversion of (S)-3-amino-1,2-dihydroxypropane 1 to (R)-1-bromo-2,3-dihydroxypropane 3.

Figure 5:
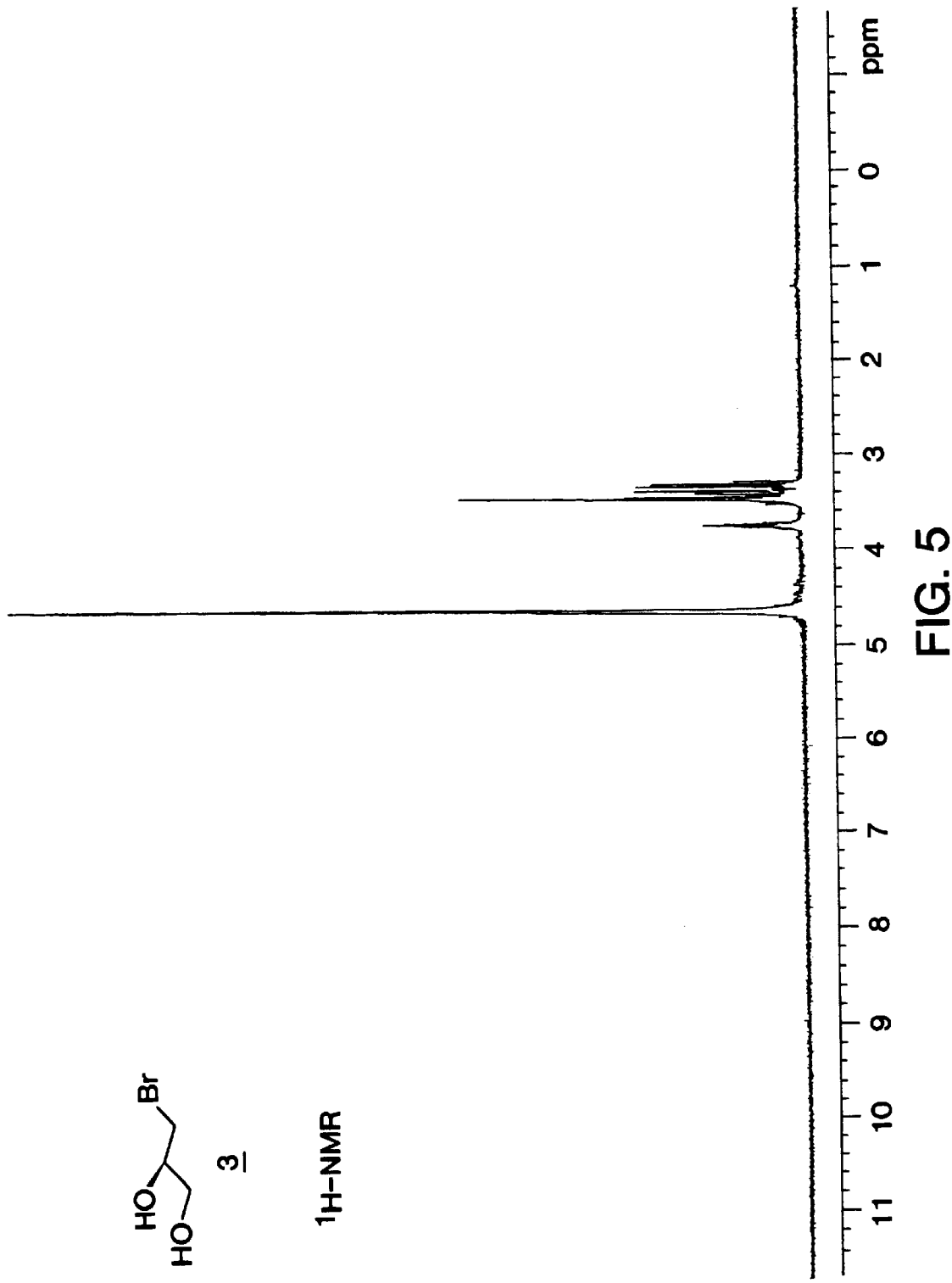
FIG. 5 is a $^1$H-NMR profile of 1-bromo-2,3-dihydroxypropane (3).
Figure 6:
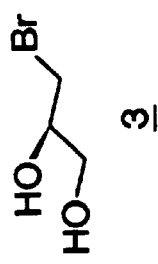
FIG. 6 is a 13C-NMR profile of 3-bromo-2,3-dihydroxypropane (3).
Figure 6:
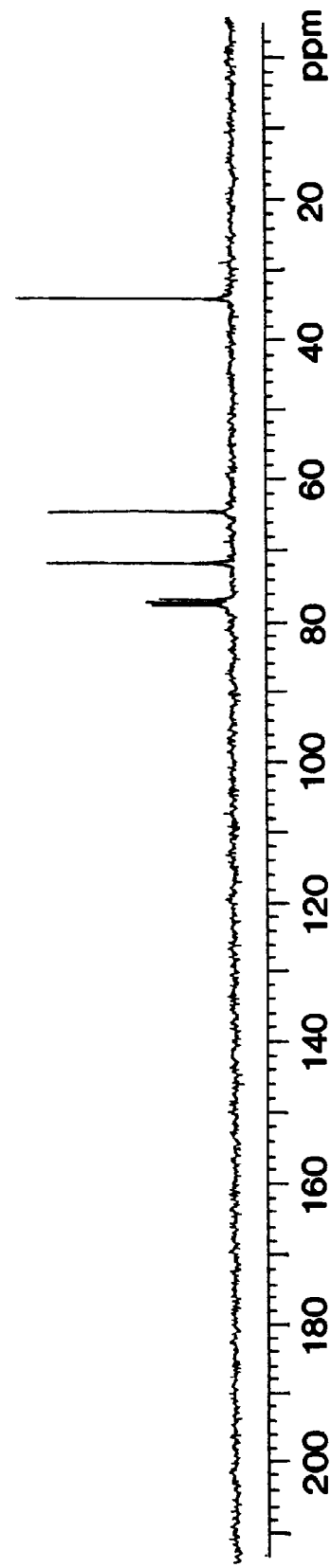

(S)-3-Amino-1,2-dihydroxypropane isopropylidene acetal (11) (0.10 g) was dissolved in 4.5 ml water. Hydrogen bromide (hydrobromic acid) solution (0.5 ml, 47% aqueous solution) and 0.52 g of sodium bromide were added to the solution which was then cooled to 0° C. Sodium nitrite (0.70 g) was added to the mixture and it was stirred at room temperature for 20 hours. A sample was tested by NMR spectroscopy which indicated complete conversion of the aminodiol to the bromodiol. The mixture was neutralized by sodium bicarbonate, then most of the water was removed by rotary evaporation and the residue was extracted in chloroform. The chloroform phase was dried over sodium sulfate; removal of the solvent gave the bromodiol 3 as a yellow liquid. The yield was 0.095 g (80%). $[\alpha]_{589}$=−4.00 (CHCl$_3$, c=1), $^1$H-NMR (CDCl$_3$, 300 MHZ) δ 3.93 (m, 1H), 3.77 (dd, 1H, J=11.4 and 3.6 Hz), 3.66 (dd, 1H, J=11.4 and 6.0 Hz), 3.85–3.46 (m, 2H). C-NMR (CDCl$_3$ 75 MHZ) δ 71.44, 64.27, 34.62. FIGS. 5 and 6 show the 1H-NMR and 13C-NMR profiles, respectively, for 3.

EXAMPLE 3

This Example shows the conversion of (S)-3-amino-1,2-dihydroxypropane isopropylidene acetal 11 to (S)-1-chloro-2,3-dihydroxypropane 3. This was done as described for the preparation of the corresponding bromo-compound above except that the sodium bromide was replaced by sodium chloride and hydrochloric acid was used instead of hydrobromic acid.

(S)-3-Amino-1,2-dihydroxypropane isopropylidene acetal (11) (0.10 g) was dissolved in 4.5 ml water. Hydrochloric acid solution (0.5 ml, 37% aqueous solution) and 0.52 g of sodium bromide chloride were added to the solution which was then cooled to 0° C. Sodium nitrite (0.70 g) was added to the mixture and it was stirred at room temperature for 20 hours. A sample was tested by NMR spectroscopy which indicated complete conversion of the aminodiol to the chlorodiol. The mixture was neutralized by sodium bicarbonate, then most of the water was removed by rotary evaporation and the residue was extracted in chloroform. The chloroform phase was dried over sodium sulfate; removal of the solvent gave the chlorodiol 3.

EXAMPLE 4

This Example shows the conversion of (S)-3-amino-1,2-dihydroxypropane isopropylidene acetal 11 to (S)-3-amino-1,2-dihydroxypropane 4. This conversion was readily effected by treatment of the acetal (11) with 1.1 equivalents of a mineral acid in water followed by the removal of the solvent by rotary evaporation. This yielded the corresponding salt.

EXAMPLE 5

This example shows the preparation of (R)-glycidol (2) from (R)-1-bromo-2,3-dihydroxypropane (3). This conversion was readily effected by treatment of the bromodiol with a base in water which yielded the epoxyalcohol (2).

EXAMPLE 6

This example shows the preparation of (R)-3-Chloro-1,2-propanediol (12) from (S)-3-amino-1,2-dihydroxypropane isopropylidene acetal (11). The amine 11 2.62 g (0.02 mol) was dissolved in 10 ml water. Sodium chloride 8.78 g (0.15 mol) was added along with concentrated hydrochloric acid (37%) 20 ml (0.2 mol) diluted with 10 ml water. Sodium nitirte 10.4 g (0.15) was then added over a period of 10 minutes. The mixture was then stirred for 24 hours after which time an analysis of the reaction by NMR spectroscopy indicated complete conversion to the chlorodiol. The mixture was then concentrated to dryness and the product was extracted with chloroform 3 or 4 times. The extracts were combined and dried with sodium sulfate. Removal of the solvent gave the chlorodiol It as a light yellow liquid 1.81 g (82%). $[\alpha]_{589}$=–7.2 ($H_2O$, c=5), H-NMR ($D_2O$, 300 MHZ) $\delta$ppm 3.86 (m, 1H), 3.68–3.48 (m, 4H). $^{13}$C-NMR ($CDCl_3$ 75 MHZ) $\delta$ppm 71.7, 63.6, 45.8. All products were >99.5% optically pure by chiral G.C.

It is intended that the foregoing description be only illustrative of the present invention and that the present invention be limited only by the hereinafter appended claims.

We claim:

1. A process for preparing a protected 3-amino-1,2-dihydroxypropane acetal in a Hoffman rearrangement reaction mixture, having the formula:

wherein $R_1$ and $R_2$ are protecting groups which can be combined which comprises reacting a protected 1,2-dihydroxybutryamide in a reaction mixture, having the formula:

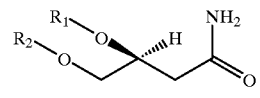

wherein $R_1$ and $R_2$ are the same protecting groups with a hypohalite in the presence of a base in a solvent for the reaction mixture to produce the protected 3-amino-1,2-dihydroxypropane acetal.

2. The process of claim 1 wherein the protected 3,4-dihydroxybutyramide is produced from 3,4-dihydroxybutyramide in a reactive mixture comprising an acid and a protecting group in a solvent for the reaction to produce the protected 3,4-dihydroxybutyramide.

3. The process of claim 2 wherein the 3,4-dihydroxybutyramide is produced from 3-hydroxy-γ-butyrolactone in a reactive mixture comprising ammonia in a solvent for the reaction to produce the protected 3,4-dihydroxybutyramide.

4. The process of claims 1 or 3 wherein the 3-hydroxy-γ-butyrolactone and protected 3-amino-1,2-dihydroxypropane acetal produced are chiral.

5. The process of claim 1 wherein the protecting group is selected from the group consisting of alkyloxy, aryloxy, acyloxy, halo, sulfonyloxy, sulfate, phosphate, saccharide and combinations thereof.

6. The process of claim 1 wherein the protecting group is an acetal selected from the group consisting of alkylidene, arylidene, acylidene and combinations thereof.

7. The process of claim 1 wherein the protecting group is a geminal dimethoxy-acetal.

8. The process of claim 1 wherein in addition the protected 3-amino-1,2-dihydroxypropane acetal is reacted to an acid to produce 1-amino-2,3-dihydroxypropane.

9. The process of claim 1 wherein in addition the protected 3-amino-1,2-dihydroxypropane acetal is reacted with a halide source and a nitrite in the presence of an acid to produce 1-halo-2,3-dihydroxypropane.

10. The process of claim 9 wherein in addition the 1-halo-2,3-dihydroxypropane is reacted with a base to form chiral 2,3-epoxy-1-hydroxypropane.

11. The process of claim 9 wherein the protected 3-amino-1,2-dihydroxypropane acetal and the 1-halo-2,3-dihydroxypropane produced are chiral.

12. The process of claim 9 wherein halo is selected from the group consisting of Cl, Br, I and F.

13. A process which comprises:
(a) reacting 3-hydroxy-γ-butyrolactone with ammonia to produce 3,4-dihydroxybutyramide;
(b) reacting the 3,4-dihydroxybutyramide with acetone and dimethyoxypropane in the presence of an acid to produce 3,4-dihydroxybutyramide isopropylidene acetal; and
(c) reacting the 3,4-dihydroxybutyramide isopropylidene acetal with an hypohalite in the presence of a base to produce 3-amino-1,2-dihydroxypropane isopropylidene acetal.

14. The process of claim 13 wherein in addition the 3-amino-1,2-dihydroxypropane isopropylidene acetal is reacted with an acid to produce 1-amino-2,3-dihydroxypropane.

15. The process of claim 13 or 14 wherein the 3-hydroxy-γ-butyrolactone and the 3-amino-1,2-dihydroxypropane isopropylidene acetal produced are chiral.

16. The process of claim 13 wherein in addition the 3-amino-1,2-dihydroxypropane isopropylidene acetal is reacted with a halide source and nitrite in the presence of an acid to produce 1-halo-2,3-dihydroxypropane.

17. The process of claim 16 wherein in addition the 1-halo-2,3-dihydroxypropane is reacted with a base to form chiral 2,3-epoxy-1-hydroxypropane.

18. The process of claim 16 wherein the 3-amino-1,2-dihydroxypropane isopropylidene acetal and the 1-halo-2,3-dihydroxypropane are chiral.

19. The process of claim 16 wherein halo is selected from the group consisting of Cl, Br, I and F.

* * * * *

UNITED STATES PATENT AND TRADEMARK OFFICE
CERTIFICATE OF CORRECTION

PATENT NO. : 6,040,464
DATED : March 21, 2000
INVENTOR(S) : Rawle I. Hollingsworth and Guijun Wang It is certified that error appears in the above-indentified patent and that said Letters Patent is hereby corrected as shown below:

On the title page: Item [56]

under "Other Publications", second column, line 8, "(1988), Jun." should be -- (1988), July --.

Column 2, line 62, "1,2-dihydroxybutryamide" should be -- 1,2-dihydroxybutyramide --.

Column 3, line 41, "1H-NMR" should be -- $^1$H-NMR --.

Column 3, line 50, "13C-NMR" should be -- $^{13}$C-NMR --.

Column 3, line 66, "dihydroxybutryamide" should be -- dihydroxybutyramide --.

Column 5, line 59, "butryamide" should be -- butyramide --.

Column 7, line 30, "Roffman" should be -- Hoffman --.

Column 8, line 14, "show the H-NMR and 13C-" should be -- show the $^1$H-NMR and $^{13}$C- --.

UNITED STATES PATENT AND TRADEMARK OFFICE
CERTIFICATE OF CORRECTION

PATENT NO. : 6,040,464
DATED : March 21, 2000
INVENTOR(S) : Rawle I. Hollingsworth and Guijun Wang It is certified that error appears in the above-indentified patent and that said Letters Patent is hereby corrected as shown below:

Column 8, line 25, "mp 54-560C" should be -mp 54-56°C-.

Column 8, line 30, "H-NMR (CD" should be $-^1$H-NMR (CD -.

Column 8, line 36, after "respectively, for", -11.- should be inserted.

Column 8, line 41, "dihydroxypropane 1 to" should be dihydroxypropane 11 to-.

Column 8, line 59, "C-NMR" should be $-^{13}$C-NMR-.

Column 8, line 60, "1H-NMR and 13C-" should be $-^1$H-NMR and $^{13}$C- --.

Column 9, line 46, "nitirte" should be -nitrite-.

Column 9, line 54, "chlorodiol It as a" should be -chlorodiol 12 as a -.

Column 9, line 55, "H-NMR (D$_2$O, 300" should be $-^1$H-NMR (H$_2$O 300 --.

Column 10, line 9 (Claim 1), "dihydroxybutryamide" should be -dihydroxybutyramide-.

UNITED STATES PATENT AND TRADEMARK OFFICE
CERTIFICATE OF CORRECTION

PATENT NO. : 6,040,464
DATED : March 21, 2000
INVENTOR(S) : Rawle I. Hollingsworth and Guijun Wang It is certified that error appears in the above-indentified patent and that said Letters Patent is hereby corrected as shown below:

Column 10, line 61 (Claim 13), "dimethyoxypropane" should be -- dimethoxypropane --.

Signed and Sealed this

Thirteenth Day of March, 2001

Attest:

NICHOLAS P. GODICI

*Attesting Officer*  *Acting Director of the United States Patent and Trademark Office*